US00PP37233P2

(12) United States Plant Patent
Ranney et al.

(10) Patent No.: US PP37,233 P2
(45) Date of Patent: Jan. 27, 2026

(54) ***HYDRANGEA* PLANT NAMED 'NCHQ1'**

(50) Latin Name: *Hydrangea quercifolia*
Varietal Denomination: NCHQ1

(71) Applicant: North Carolina State University, Raleigh, NC (US)

(72) Inventors: Thomas Green Ranney, Arden, NC (US); Andra Windorf Nus, Arden, NC (US); Irene Palmer, Arden, NC (US); John Tyler Nix, Arden, NC (US); Nathan Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/245,284

(22) Filed: Jun. 21, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Shubo Zhou
*Assistant Examiner* — Zachariah Allan Kay

(57) ABSTRACT

A new and distinct cultivar of *Hydrangea* plant named 'NCHQ1' is disclosed, characterized by large terminal panicles having showy white sepals fading to green with maturity. Plants are highly floriferous, compact and densely branched. Mature height and width of plants is approximately three to four feet. Fall foliage is bright burgundy. The new cultivar is a *Hydrangea*, normally used for outdoor ornamental purposes.

3 Drawing Sheets

Latin name of the genus and species: *Hydrangea quercifolia.*

Cultivar denomination: 'NCHQ1'.

BACKGROUND OF THE INVENTION

This new *Hydrangea* cultivar was developed through a breeding program in Mills River, North Carolina to invent new cultivars with compact habits and profuse flowering. 'NCHQ1' was selected from a group of seedlings derived from the open pollination of an unpatented, unnamed *Hydrangea quercifolia* breeding line. The pollen parent is unknown. The cross resulting in this new cultivar was made during 2011. 'NCHQ1' was identified as a potentially interesting selection in 2012, at a research nursery in Mills River, North Carolina.

Asexual propagation of the new cultivar 'NCHQ1' by stem cuttings was first performed during July 2015 at a research nursery in Mills River, North Carolina. Subsequent propagation has shown that the unique features of this cultivar are stable and reproduced true to type in three successive propagation cycles.

Plants of the new cultivar were first disclosed to third parties Jun. 25, 2024, in the United States. Plants were shown at an invitational event in Grand Haven, MI. This disclosure was made directly by the inventor or one who obtained the claimed invention directly or indirectly from the inventor. This and all public disclosures made between Jun. 25, 2024, and the filing of this application fall within the exception allowed under 102(b)(1).

SUMMARY OF THE INVENTION

The cultivar 'NCHQ1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCHQ1' These characteristics in combination distinguish 'NCHQ1' as a new and distinct *Hydrangea* cultivar:

1. Compact, densely branched habit.
2. Mature height and width of 3 to 4'.
3. Large (10 to 15 cm in length) terminal flower panicles.
4. High floriferousness.
5. Showy white flower (sepal) color which fades to green.
6. Bright burgundy fall foliage color.

PARENT COMPARISONS

Plants of the new cultivar *Hydrangea* 'NCHQ1' could not be compared to plants of the seed or pollen parents due to insufficient data.

COMMERCIAL COMPARISON

Plants of the new cultivar 'NCHQ1' are comparable to the commercial cultivar *Hydrangea quercifolia* 'Snow Queen', unpatented. The two *Hydrangea* cultivars are similar in most horticultural characteristics, however, the new cultivar 'NCHQ1' differs in the following:

1. Plants of the new cultivar are smaller at maturity than plants of this comparator.
2. Plants of the new cultivar have more dense branching habits, while plants of this comparator have less dense branching habits.
3. Sepal color of the new cultivar ages to green, while the sepal color of this comparator ages to pink.

BRIEF DESCRIPTION OF THE PHOTOGRAPHS

This new *Hydrangea* is illustrated by the accompanying photographs which show the plant's form and foliage. The colors shown are as true as can be reasonably obtained by conventional photographic procedures. Colors in the photographs may differ slightly from the color values cited in the detailed botanical description, which accurately describe the colors of the new *Hydrangea*.

DETAILED BOTANICAL DESCRIPTION

Figure 1:
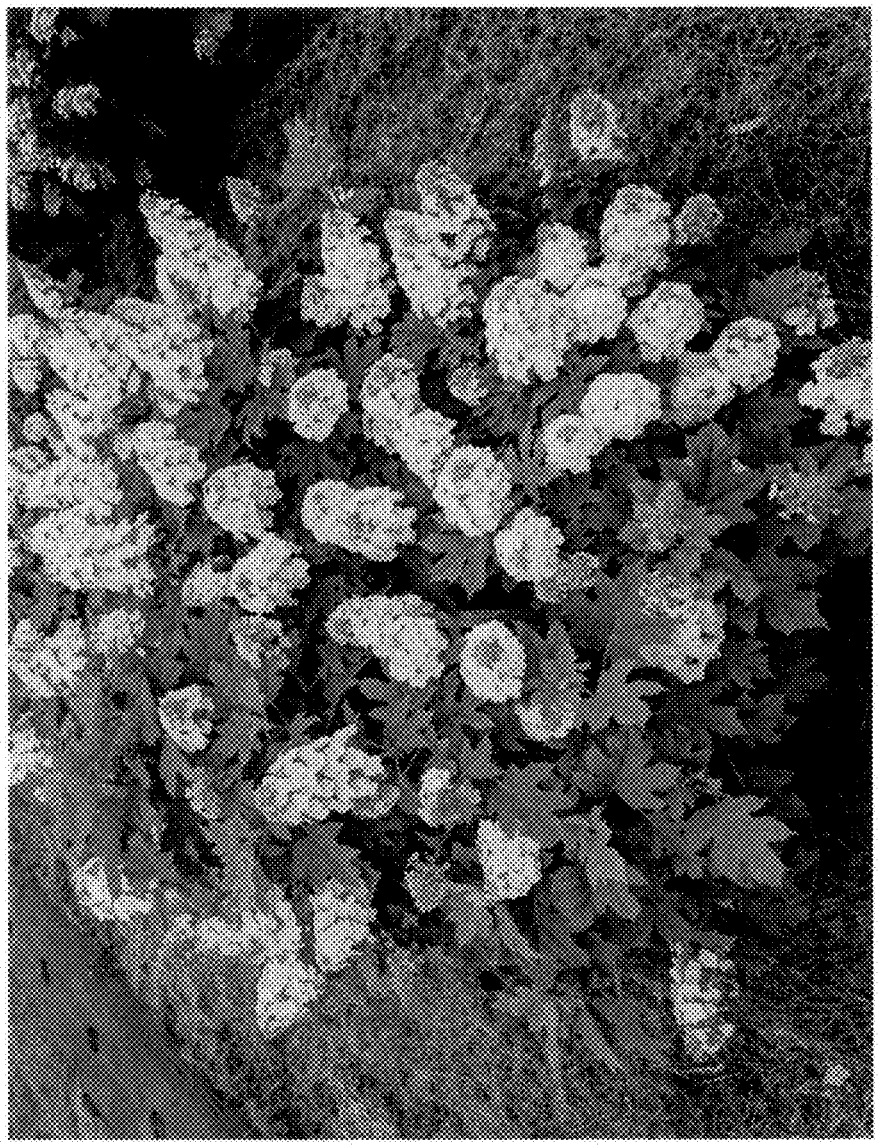
FIG. 1 is a photograph showing the compact habit of 'NCHQ1' in the summer of 2023 in Grand Haven, Michigan.
Figure 2:
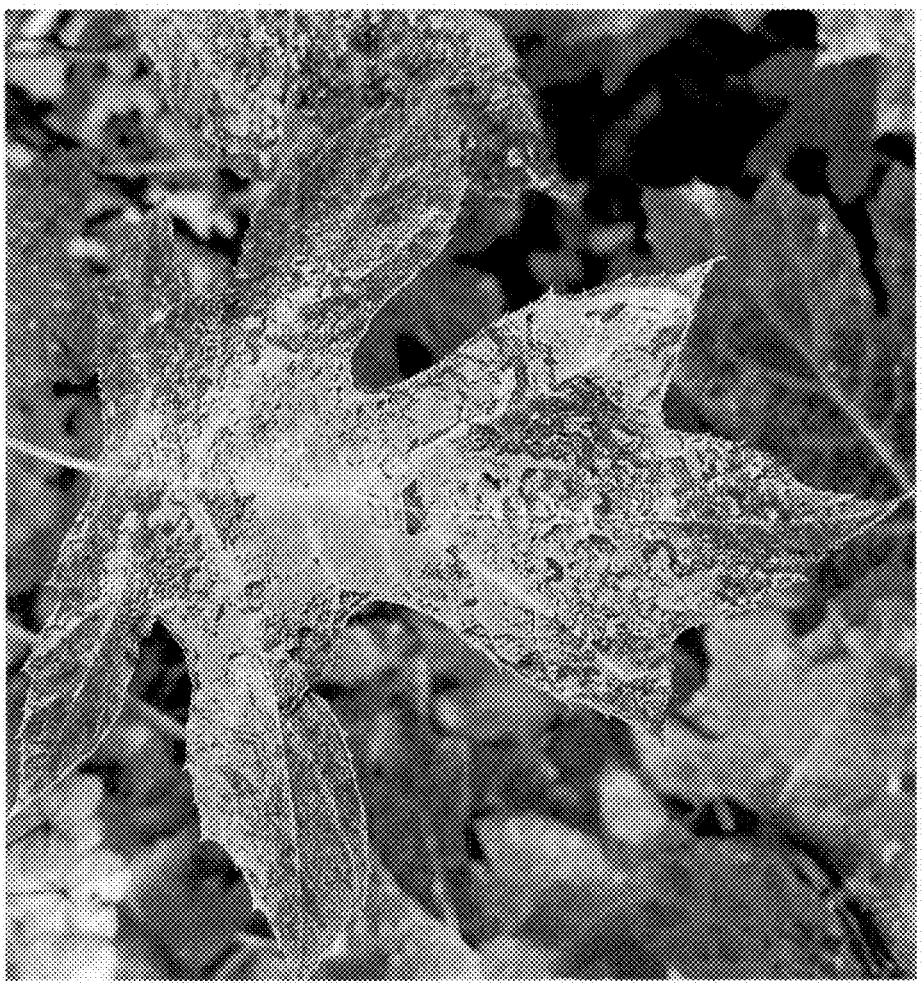
FIG. 2 is a photograph showing the reddish fall color of the foliage of 'NCHQ1' in the fall of 2024 in Arden, North Carolina.
Figure 3:
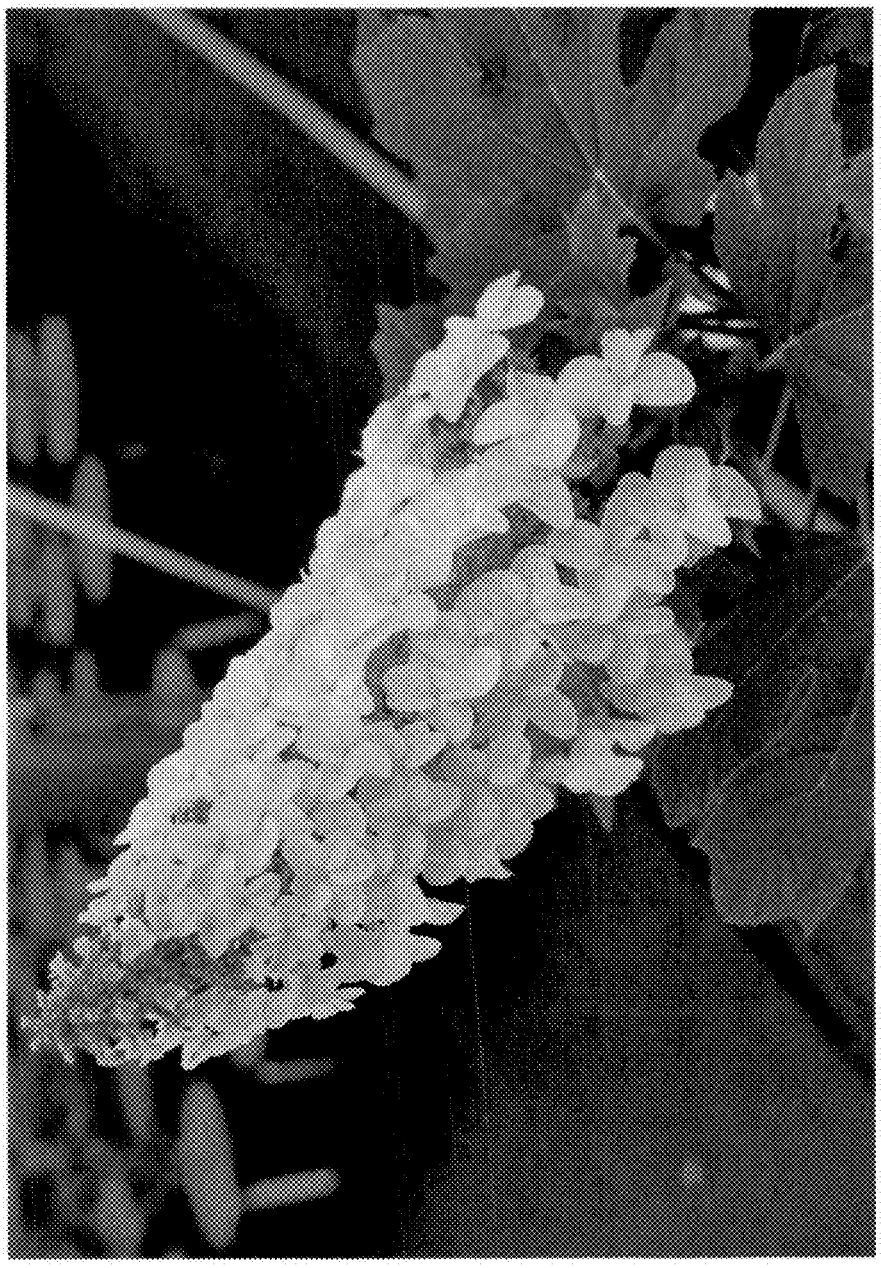
FIG. 3 is a photograph showing the dense inflorescences with numerous sterile florets of 'NCHQ1' in summer of 2022 in Grand Haven, Michigan.

The following is a detailed description of the botanical characteristics of the new and distinct *Hydrangea* cultivar known by the denomination 'NCHQ1'. The detailed description was taken on a three-year-old container-grown plant in Mills River, North Carolina in 2024 with supplemental data taken from a five-year-old landscape plant in Arden, North Carolina. All colors cited herein refer to The Royal Horticultural Society Colour Chart (The Royal Horticultural Society (R.H.S.), London, 2015, Sixth Edition). Where specific dimensions, sizes, colors, and other characteristics are given, it is to be understood that such characteristics are approximations or averages set forth as accurately as practicable.

Botanical classification: *Hydrangea quercifolia* 'NCHQ1'.

PROPAGATION

Type of propagation typically used: Softwood cuttings.

PLANT

Age of plant described: 3 years.
Plant type: Flowering shrub.
Growth habit: Rounded, upright.
Plant spread: 90 to 120 cm.
Plant height: 90 to 120 cm.
Stems, shoots, branches:
- *Shoots* (*current year's growth*).—Shoot length: Average 6.5 cm (Range 3.0 cm to 12 cm). Shoot diameter: About 0.7 cm. Color: RHS Greyed-Orange 166D. Texture: Densely pubescent.
- *Shoots* (*prior year's growth*).—Stem length: About 7 cm. Stem diameter: About 0.7 cm. Color: RHS Brown 199B with exfoliating strips of N199B. Texture: Pubescent to exfoliating.
- *Branches* (*woody branches* 2-4 *years old*).—Branch length: About 25 cm. Branch diameter: Average 1.1 cm (0.8 to 1.5 cm). Color: RHS Brown 199A. Texture: Exfoliating.

Internode length: 1.0 to 9.0 cm.

FOLIAGE

Leaf:
- *Type*.—Simple.
- *Persistence*.—Deciduous.
- *Arrangement*.—Opposite.
- *Shape*.—Roughly ovate in outline with five pinnate lobes.
- *Length of lamina*.—Average 12.9 cm (7.5 to 20.5 cm).
- *Width*.—Average 13.3 cm. (8.0 to 19.5 cm).
- *Apex*.—Acuminate.
- *Base*.—Truncate to subcordate.
- *Margin*.—Five-lobed with serrulate margins.
- *Color, emerging foliage*.—Upper: Near RHS Green 138B. Lower: Near RHS Yellow Green 145D.
- *Color, mature foliage*.—Upper: RHS Green 137A. Lower: RHS Green 138B.
- *Texture, emerging foliage*.—Upper: Pubescent. Lower: Pubescent.
- *Texture, emerging foliage*.—Upper: Sparsely pubescent. Lower: Pubescent.
- *Venation*.—Pinnate.
- *Vein color, emerging foliage*.—RHS Yellow-Green 145A.
- *Vein color, mature foliage*.—RHS Yellow-Green 145C.
- *Leaf attachment*.—Petiolate.

Petiole:
- *Length*.—Average 7.7 cm (3.5 to 13 cm).
- *Diameter*.—About 0.1 to 0.2 cm.
- *Color*.—Near RHS Yellow-Green 146D.
- *Texture*.—Pubescent.

FLOWER

Inflorescence:
- *Description*.—Flowers arranged in terminal, broadly pyramidal panicles, composed of fertile and sterile flowers.
- *Number of flowers per inflorescence*.—About 1600 individual fertile flowers and about 100 individual sterile flowers.
- *Flowering season*.—May to June in Mills River, NC.
- *Fragrance*.—Light, sweet.
- *Diameter*.—Average 1.6 cm (1.5 to 1.8 cm).
- *Height*.—Average 1.3 cm (1.2 to 1.4 cm).

Inflorescence, terminal:
- *Length*.—10 to 15 cm.
- *Diameter at base*.—10 to 15 cm.

Inflorescence, axillary:
- *Length*.—3 to 10 cm.
- *Diameter at base*.—5 to 10 cm.

Flower buds:
- *Shape*.—Round.
- *Length*.—0.18 to 0.2 cm.
- *Diameter*.—0.18 to 0.2 cm.
- *Color*.—A mixture of RHS Yellow-Green 157B and Yellowish-White 158C.
- *Texture*.—Glabrous.

Sterile flowers:
- *Description*.—Single flowers with 4-5 sepals and inconspicuous reproductive parts.
- *Diameter*.—About 2.0 to 2.5 cm.
- *Height*.—About 0.15 cm.

Sepals:
- *Number*.—4, occasionally 5.
- *Length*.—About 1.0 cm.
- *Width*.—About 0.8 to 1.2 cm.
- *Color*.—RHS Greenish-White 157D, fading to Yellow-Green 145B.
- *Texture*.—Glabrous.
- *Apex*.—Rounded.
- *Margin*.—Entire.

Fertile flowers:
- *Diameter*.—About 0.5 cm.

*Height*.—About 0.3 cm.

Peduncle:

*Length*.—10 to 15 cm.

*Diameter*.—0.2 to 0.5 cm.

*Color*.—RHS Yellow-Green 147D.

*Texture*.—Pubescent, with RHS Brownish-Orange 165B hairs.

Pedicels, sterile flowers:

*Length*.—About 0.3 to 1.0 cm.

*Diameter*.—About 0.1 cm.

*Color*.—RHS Yellow-Green 145D.

*Texture*.—Glabrous.

Pedicels, fertile flowers:

*Length*.—About 0.1 cm.

*Diameter*.—Less than 0.05 cm.

*Color*.—RHS Yellow-Green 145B.

*Texture*.—Glabrous.

REPRODUCTIVE ORGANS

Fertile flowers:

Gynoecium:

*Pistil number*.—1.

*Pistil length*.—0.15 cm.

*Stigma shape*.—Rounded, 2-lobed.

*Stigma color*.—RHS Yellow-Green 157C.

*Style length*.—About 0.1 cm.

*Style color*.—RHS White 155C.

Androecium:

*Stamen number*.—10.

*Anther size*.—Less than 0.05 cm.

*Anther color*.—RHS White NN155A.

*Amount of pollen*.—Normal.

*Pollen color*.—RHS White NN155A.

OTHER CHARACTERISTICS

Fruit and seed: None observed.

Disease/pest resistance: Neither resistance nor susceptibility to other diseases and pests of *Hydrangea* have been observed.

Cold hardiness: At least USDA zone 6b; testing has not been completed in colder zones.

What is claimed is:

1. A new and distinct cultivar of *Hydrangea* plant named 'NCHQ1' as herein illustrated and described herein.

* * * * *